United States Patent [19]

Mandai et al.

[11] 4,214,112

[45] Jul. 22, 1980

[54] PROCESS FOR PREPARING OLEFIN OLIGOMER

[75] Inventors: Hiroshi Mandai, Chiba; Anri Tominaga, Funabashi; Yoshikazu Yoshimura, Chiba; Hiroshi Isa, Yachiyo, all of Japan

[73] Assignee: The Lion Fat & Oil Co., Ltd., Tokyo, Japan

[21] Appl. No.: 24,205

[22] Filed: Mar. 27, 1979

[30] Foreign Application Priority Data

Mar. 27, 1978 [JP] Japan ................................. 53-35231

[51] Int. Cl.$^2$ ............................................. C07C 3/18
[52] U.S. Cl. ..................................... 585/532; 585/531
[58] Field of Search ................................ 585/531, 532

[56] References Cited

U.S. PATENT DOCUMENTS

| | | | |
|---|---|---|---|
| 3,769,363 | 10/1973 | Brennan | 585/532 |
| 3,952,071 | 4/1976 | Isa et al. | 585/532 |
| 3,997,622 | 12/1976 | Isa et al. | 585/532 |
| 3,997,623 | 12/1976 | Isa et al. | 585/532 |
| 4,031,159 | 6/1977 | Mandai et al. | 585/532 |
| 4,066,715 | 1/1978 | Isa et al. | 585/532 |

*Primary Examiner*—C. Davis
*Attorney, Agent, or Firm*—Armstrong, Nikaido, Marmelstein & Kubovcik

[57] ABSTRACT

A process for producing an olefin oligomer comprising polymerizing olefin having not less than 6 carbon atoms in the presence of a catalyst consisting essentially of (a) aluminum halide, (b) polyhydric alcohol derivative of which alcohol the hydrogen atoms of the entire hydroxyl groups are substituted with either one or both of alkyl and acyl groups and (c) a nickel compound or cobalt compound is provided. Thus, an olefin oligomer having a narrow distribution of the polymerization degree and good properties can be obtained with a high selectivity by using a catalyst capable of being easily handled.

9 Claims, No Drawings

PROCESS FOR PREPARING OLEFIN OLIGOMER

The present invention relates to a process for producing olefin oligomers from olefins having not less than 6 carbon atoms. More specifically, it relates to a process for producing olefin oligomers from olefins having not less than 6 carbon atoms by using a specified catalyst which can be easily handled and can produce the trimer with a high yield or selectivity.

It is known in the art that long-chain olefins are oligomerized to form liquid oligomers suitable for use as a lubricating oil. For instance, it has been proposed in U.S. Pat. No. 3,769,363 that olefins having from 6 to 12 carbon atoms are oligomerized in the presence of a catalyst containing, as a principal component, boron trifluoride and, as a promoter, an aliphatic carboxylic acid having at least 3 carbon atoms. It has been also proposed in U.S. Pat. Nos. 3,952,071 and 3,997,623 that an olefin having 6 or more carbon atoms is oligomerized in the presence of a catalyst consisting of an aluminum halide and the ether or ester of a polyhydric alcohol. Furthermore, it has been proposed in U.S. Pat. No. 3,997,622 that an olegin having more than 6 carbon atoms is oligomerized in the presence of (a) polyhydric alcohol derivatives, (b) aluminum halide and (c) metallic aluminum powder.

However, although the oligomerization process in which boron trifluoride and an aliphatic carboxylic acid are used as a catalyst has the advantage that the trimer can be produced with a high selectivity, it has the disadvantages that, since the gaseous boron trifluoride must be used, the handling of the catalyst is troublesome, and also, that control of the temperature is not easy due to the low temperature reaction of from 0° C. to 20° C.

The oligomerization process in which an aluminum halide and the ether or ester of the polyhydric alcohol are used as a catalyst has the disadvantages that the yield of the desired product becomes low due to the low selectivity and also that the viscosity of the product becomes high. This process further has the problems that, due to the presence of halogen or halogenated products in the oligomer, when the crude oligomerization products are distilled in order to remove non-reacted olefin and dimers, the apparatus are corroded, and the hydrogenation catalysts are deteriorated during the subsequent hydrogenation operation of the oligomer.

The oligomerization process in which (a) polyhydric alcohol derivatives, (b) aluminum halide and (c) metallic aluminum powder are used as a catalyst has still the disadvantages that the yield is not satisfactory due to the low selectivity of the trimer and the viscosity of the product is high.

Accordingly, the objects of the present invention are to obviate the aforementioned disadvantages of the prior arts and to provide a process for producing an olefin oligomer having a narrow distribution of the polymerization degree and good properties, with a high yield or selectivity, by using a catalyst which can be easily handled.

In accordance with the present invention, there is provided a process for producing an olefin oligomer comprising polymerizing at least one olefin having not less than 6 carbon atoms in the presence of a catalyst consisting essentially of (a) at least one aluminum halide, (b) at least one polyhydric alcohol derivative of which alcohol the hydrogen atoms of the entire hydroxyl groups are substituted with either one or both of alkyl and acyl groups and (c) at least one compound selected from the group consisting of nickel compounds and cobalt compounds.

The olefins used, as a starting material, in the present invention include those having 6 or more carbon atoms, and preferably 6 through 20 carbon atoms. Examples of such olefins are hexane-1, octene-1, nonene-1, decene-1, dodecene-1, tridecene-1, tetradecene-1, 2-ethyloctene-1, 2-methylnonene-1, octene-2, nonene-2, decene-2, dodecene-2, tridecene-2, octene-3, decene-3, dodecene-3 and the like.

The aluminum halides used, as the component (a) of the catalyst, in the present invention include aluminum chloride, aluminum bromide, aluminum iodide and mixture thereof.

The polyhydric alcohol derivatives used, as the component (b) of the catalyst, in the present invention include, for example, polyalkylethers, polyesters, etheresters and polyetheresters, of ethylene glycol, glycerine, trimethylol propane, neopentyl glycol, pentaerythritol, 1,2-propanediol, 1,3-propanediol, 1,4-butanediol, 1,5-pentanediol, diethylene glycol, triethylene glycol and the like. Examples of such polyhydric alcohol derivatives are ethylene glycol dimethyl ether, ethylene glycol diethyl ether, diethylene glycol dimethyl ether, triethylene glycol dicapryl ether, propylene glycol methyl ethyl ether, ethoxyethyl acetate, butoxypropyl acetate, methoxyethyl propionate, 4-methoxybutyl caproate, ethylene glycol diacetate, ethylen glycol dicaprylate, propylene glycol dipropionate, 1,3-diacetoxy propane, 1,4-diacetoxy pentane, trans-1,4-diacetoxy butene, 1,5-diacetoxy pentane, diethylene glycol diacetate, dibutylene glycol dipropionate, triethylene glycol didodecanate, pentaerythritol tetraacetate and the like. These polyhydric alcohol derivatives are obtained by replacing all hydrogen atoms of the entire hydroxyl group of the polyhydric alcohol with either one or both of alkyl and acyl groups, each preferably having 1 to 20 carbon atoms.

The amount of the polyhydric alcohol derivatives, i.e. the component (b) of the catalyst, used in the present invention is within the range of from 0.4 to 1.5, and preferably from 0.6 to 1.3, and more preferably from 0.8 to 1.2 equivalents, based on 1.0 equivalent of the component (a) (i.e. the aluminum halide) of the catalyst. When the amount of the component (b) of the catalyst is less than 0.4 chemical equivalent, based on 1.0 equivalent of the component (a) of the catalyst, the selectivity of the trimer is unpreferably decreased and the content of the product having a high polymerization degree is unpreferably increased. On the other hand, when the amount of the component (b) of the catalyst is more than 1.5 equivalents, based on 1.0 equivalent of the component (a), the oligomerization time becomes unpreferably long.

By the term "1.0 equivalent of the polyhydric alcohol derivatives" is meant the quotient of 1.0 mol divided by the number of the hydroxyl groups of the polyhydric alcohol and by the term "1.0 equivalent of the aluminum halide" is meant 1.0 mol of the aluminum halide.

The nickel compounds and the cobalt compounds used, as the component (c) of the catalyst, in the present invention include, for example, nickel compounds such as nickel carbonate, nickel tetracarbonyl, nickel nitrate, nickel monoxide, trinickel tetroxide, nickel sequioxide, nickel hydroxide, nickel sulfide, nickel sulfate, nickel acetate, nickel oleate, nickel stearate, nickel diatomaceous earth, nickel chloride, nickel acetylacetonate, nickel peroxide and the like, and cobalt compounds such as cobalt carbonate, dicobalt octacarbonyl, cobalt chloride, cobalt nitrate, cobalt oxide, cobalt hydroxide, cobalt sulfide, cobalt sulfate, cobalt acetate, cobalt oleate, cobalt acetylacetonate and the like. These nickel and cobalt compounds can be used alone or in any combination thereof.

The amount of the nickel and/or cobalt compounds, i.e. the component (c) of the catalyst, used in the present invention is within the range of from 0.0001 to 2.0 atoms, and preferably from 0.001 to 1.5 atoms, in terms of nickel and/or cobalt atoms, based on 1.0 atom of the aluminum contained in the component (a) of the catalyst. When the amount of the component (c) of the catalyst is less than 0.0001 atom, based on 1.0 atom of the aluminum contained in the component (a) of the catalyst, the satisfactory improvement in the selectivity of the trimer is not observed. Contrary to this, when the amount of the component (c) of the catalyst is more than 2.0 atoms, based on 1.0 atom of the aluminum contained in the component (a) of the catalyst, the reaction tends to be difficult to proceed, the yield (or conversion) becomes low.

Furthermore, in accordance with another embodiment of the present invention, the olefin is polymerized in the presence of a catalyst consisting essentially of (a) at least one aluminum halide, (b) at least one said polyhydric alcohol derivative, (c) at least one compound selected from the nickel compounds and the cobalt compounds and (d) metallic aluminum powder. The preferable amount of the metallic aluminum powder present in the catalyst is within the range of from 0.1 to 5.0 atoms based on 1.0 atom of aluminum contained in the aluminum halide. In the case where such amounts of the metallic aluminum powder are present in the catalyst, the olefin oligomer containing no substantial halogenated products can be obtained. It is known that, when halogenated products are present in the olefin oligomer, hydrogenation catalysts are deteriorated during the hydrogenation step of the olefin oligomer.

The polymerization or oligomerization process according to the present invention can be carried out in the absence of or in the presence of solvent. Examples of the suitable solvents are hydrocarbons such an n-pentane, n-hexane, isooctane, n-octane and the like, and chlorinated hydrocarbons such as trichloroehtane, tetrachloroethane, 1,2-dichloroethane and the like. The amount of the catalyst used in the present invention is preferably selected from the range of from 1 to 6% by weight in terms of the aluminum halide (i.e. the component (a) of the catalyst), based on the weight of the starting olefin. When the amount of the catalyst is less than 1% by weight (in terms of the weight of the aluminum halide), based on the weight of the olefin, the reaction tends to be difficult to occur. On the other hand, when the amount of the catalyst is more than 6% by weight (in terms of the weight of the aluminum halide), based on the weight of the olefin, no substantial increase in the effect of the present invention is observed although such amount of the catalyst can be used.

The reaction temperature of the present process is preferably within the range of from 40° to 70° C., and more preferably from 60° to 150° C. This is because, when the reaction temperature is more than 170° C., the viscosity index of the product tends to become low, and because, when the reaction temperature is less than 40° C., this would tend to considerably lower the reactivity.

The present process is, in general, carried out, for example, under pressure such as, for example, 1 through 10 atm., or under reduced pressure.

According to the present invention, since the Lewis acid used as a catalyst is not gaseous boron trifluoride (which is used in the prior art processes) but solid aluminum halides, there are the advantages that the handling of the catalyst is easy and is not dangerous, and therefore, the construction cost of the production plant becomes relatively cheap.

In addition, according to the present invention, the content of the trimer contained in the desired product, i.e. the oligomer having 20 or more carbon atoms, is high and the yield of the desired product itself is also good. Furthermore, since the catalyst system used in the present invention can be easily separated from the olefins and the resultant polymers at around room temperature and no substantial decrease in the activity of the separated catalyst is observed, there are the advantages that the catalyst can be recovered and recycled to the subsequent operation.

The present invention will be further illustrated by, but is by no means limited to, the following Examples.

EXAMPLES 1 to 15

Into a 1 liter glass flask provided with an agitator, each anhydrous aluminum chloride or aluminum bromide (i.e. the component (a)) and each polyhydric alcohol derivative (i.e. the component (b)) listed in Table 1, and each nickel or cobalt salt (i.e. the component (c)) listed in Table 1 were charged in the amounts shown in Table 1. After the contents of the flask was heated to the reaction temperature shown in Table 1, 500 g of each olefin listed in Table 1 were gradually dropwise added into the flask and were allowed to be oligomerized at the reaction temperature. Upon the completion of the oligomerization, the reaction mixture was allowed to stand for further 30 minutes. The olefin oligomer thus obtained was separated from the catalyst by means of a centrifugal separator and recovered.

The oligomerization test was repeated by using the residual catalyst in the same procedure as mentioned above. This olefin oligomerization was repeated five times in total by using the same catalyst in order to evaluate the period of life of the catalyst. The results obtained in the first and fifth runs are shown in Table 2.

In Examples 1 to 13 and 15, aluminum chloride is used as the component (a) and in Example 14 aluminum bromide is used. In addition, in Example 5, 1.51 g (0.5 gram atom/1 mol of AlCl$_3$) of metallic aluminum powder is also added to the catalyst system.

In Table 1, the following abbreviations are used for the compounds of the component (b) of the catalyst.

EGDA: Ethylene glycol diacetate
EGDEE: Ethylene glycol diethyl ether
EOEA: Ethoxy ethyl acetate
DAOP: 1,3-Diacetoxy propane In Table 2, "Conversion" indicates the conversion of the oligomer containing the dimer and the higher polymerization products present in the reaction product, "Yield" indicates the yield of the oligomer containing the trimer and the higher polymerization products and "Composition" indicates the contents of the trimer and the high polymer containing the tetramer and the higher polymerization products present in the oligomer containing the trimer and the higher polymerization products.

As shown in Table 2 below, in Example 15 wherein the catalyst containing metallic aluminum powder in addition to the other three components (a), (b) and (c), the conversion and the yield of the trimer were substantially similar to those of the corresponding Example 1. However, since the product obtained in Example 15 contained no substantial amount of halogen or halogenated products, the deterioration of hydrogenation catalyst was not observed during the hydrogenation step of the oligomer.

TABLE 1

| Example No. | Olefin | Component (a) (g) | Component (b) Compound | Component (b) Equivalent ratio b/a | Component (c) Compound | Component (c) Atomic ratio c/a | Reaction Condition Temperature (°C.) | Reaction Condition Time (hr) |
|---|---|---|---|---|---|---|---|---|
| 1 | Decene-1 | 15.0 | EGDA | 1.05 | Nickel oxide | 0.01 | 120 | 4 |
| 2 | " | 15.0 | " | 1.00 | " | 1.5 | 120 | 6 |
| 3 | " | 15.0 | " | 1.05 | Nickel chloride | 0.3 | 130 | 5 |
| 4 | " | 15.0 | " | 1.00 | " | 3.0 | 130 | 15 |
| 5 | " | 15.0 | " | 1.00 | " | 0.00001 | 120 | 3 |
| 6 | " | 15.0 | " | 1.05 | Nickel oleate | 0.2 | 120 | 4 |
| 7 | " | 15.0 | " | 1.05 | Nickel oxide | 0.2 | 120 | 4 |
| 8 | " | 15.0 | " | 1.05 | Nickel carbonate | 0.2 | 120 | 4 |
| 9 | " | 10.0 | EGDEE | 1.15 | Nickel chloride | 0.2 | 120 | 4 |
| 10 | " | 10.0 | EOEA | 1.10 | " | 0.2 | 130 | 5 |
| 11 | Octene-1 | 15.0 | EGDA | 1.05 | " | 0.2 | 120 | 5 |
| 12 | Dodecene-1 | 15.0 | " | 1.05 | Nickel oxide | 0.2 | 120 | 5 |
| 13 | Decene-1 | 15.0 | DAOP | 1.00 | Cobalt chloride | 0.2 | 130 | 6 |
| 14 | " | 30.0* | EGDA | 1.05 | Nickel oxide | 0.01 | 120 | 4 |
| 15 | " | 15.0 | " | 1.05 | " | 0.01 | 120 | 4 |

*AlBr$_3$

TABLE 2

| Example No. | First Run Conversion (wt. %) | First Run Yield (wt. %) | First Run Composition (wt. %) Trimer | First Run Composition (wt. %) High Polymer | Fifth Run Conversion (wt. %) | Fifth Run Yield (wt. %) | Fifth Run Composition (wt. %) Trimer | Fifth Run Composition (wt. %) High Polymer |
|---|---|---|---|---|---|---|---|---|
| 1 | 95.2 | 80.0 | 70.6 | 29.4 | 94.0 | 80.3 | 71.0 | 29.0 |
| 2 | 93.2 | 81.0 | 72.3 | 27.7 | 93.0 | 81.9 | 69.8 | 30.2 |
| 3 | 94.2 | 80.0 | 69.6 | 30.4 | 94.5 | 82.9 | 65.0 | 35.0 |
| 4 | 50.2 | 81.1 | 71.9 | 28.1 | — | — | — | — |
| 5 | 97.2 | 83.1 | 45.0 | 55.0 | — | — | — | — |
| 6 | 93.9 | 80.4 | 70.8 | 29.2 | 94.5 | 80.0 | 69.9 | 30.1 |
| 7 | 94.8 | 80.2 | 71.2 | 28.8 | 95.0 | 79.6 | 70.5 | 29.5 |
| 8 | 93.9 | 78.8 | 69.8 | 30.2 | 94.5 | 78.4 | 70.0 | 30.0 |
| 9 | 95.2 | 80.8 | 69.8 | 30.2 | 94.8 | 80.7 | 67.9 | 32.1 |
| 10 | 94.8 | 80.1 | 68.9 | 31.1 | 94.1 | 79.7 | 67.9 | 32.1 |
| 11 | 95.2 | 85.3 | 70.6 | 29.4 | 95.0 | 84.4 | 69.9 | 30.1 |
| 12 | 94.8 | 77.9 | 71.0 | 29.0 | 94.0 | 78.7 | 70.9 | 29.1 |
| 13 | 91.4 | 82.7 | 65.3 | 34.7 | 90.9 | 82.9 | 64.9 | 35.1 |
| 14 | 95.5 | 82.3 | 71.9 | 28.1 | 94.1 | 80.6 | 72.0 | 28.0 |
| 15 | 95.9 | 81.4 | 72.6 | 27.4 | 95.2 | 79.8 | 72.3 | 27.7 |

What we claim is:

1. A process for producing an olefin oligomer comprising polymerizing at least one olefin having not less than 6 carbon atoms in the presence of a catalyst consisting essentially of (a) at least one aluminum halide, (b) at least one polyhydric alcohol derivative of which alcohol the hydrogen atoms of the entire hydroxyl groups are substituted with either one or both of alkyl and acyl groups and (c) at least one compound selected from the group consisting of nickel compounds and cobalt compounds.

2. A process as claimed in claim 1, wherein the amount of said component (b) of the catalyst is within the range of from 0.4 to 1.5 equivalents, based on 1.0 equivalent of said component (a) of the catalyst.

3. A process as claimed in claim 2, wherein said amount of the component (b), based on the component (a), is within the range of from 0.6 to 1.3 equivalents.

4. A process as claimed in claim 1, wherein the amount of said component (c) of the catalyst is within the range of from 0.0001 to 2.0 atoms, in terms of nickel or cobalt or a mixture thereof, based on 1.0 atom of aluminum contained in said component (a) of the catalyst.

5. A process as claimed in claim 4, wherein said amount of the component (c) is within the range of from 0.001 to 1.5 atoms, in terms of nickel or cobalt or a mixture thereof, based on 1.0 atom of aluminum contained in the component (a).

6. A process as claimed in claim 1, wherein the amount of the catalyst used in the process is within the range of from 1 to 6% by weight in terms of the aluminum halide, based on the weight of the olefin.

7. A process as claimed in claim 1, wherein the polymerization is conducted at a temperature within the range of from 40° to 170° C.

8. A process as claimed in claim 1, wherein said catalyst further contains metallic aluminum.

9. A process as claimed in claim 8, wherein the amount of said metallic aluminum is within the range of from 0.1 to 5.0 atoms based on 1.0 atom of aluminum contained in the aluminum halide.

* * * * *